(12) United States Patent
Matheson et al.

(10) Patent No.: US 9,802,879 B2
(45) Date of Patent: Oct. 31, 2017

(54) CATALYST COMPOSITIONS, METHODS OF PREPARATION THEREOF, AND PROCESSES FOR ALKOXYLATING ALCOHOLS USING SUCH CATALYSTS

(71) Applicant: SASOL (USA) CORPORATION, Houston, TX (US)

(72) Inventors: Kenneth L. Matheson, Lake Charles, LA (US); Kip Sharp, Fulshear, TX (US); Teresa L. Marino, Sulphur, LA (US); Shane F. Cutrer, Lake Charles, LA (US); Allan B. Hauser, De Ridder, LA (US); Tamra R. Weemes, Lake Charles, LA (US); Steve C. Lyons, Lake Charles, LA (US); Geoffrey Russell, Sulphur, LA (US); Qisheng Wu, Nanjing (CN); Harald Kohnz, Oberhausen (DE); Ollie M. James, Lake Charles, LA (US); Cecil C. Mercy, Lake Charles, LA (US); Herbert Olin Perkins, Orange, TX (US)

(73) Assignee: Sasol (USA) Corporation, Houston, TX (US)

( * ) Notice: Subject to any disclaimer, the term of this patent is extended or adjusted under 35 U.S.C. 154(b) by 0 days.

(21) Appl. No.: 15/317,476

(22) PCT Filed: Jun. 17, 2015

(86) PCT No.: PCT/US2015/036155
§ 371 (c)(1),
(2) Date: Dec. 9, 2016

(87) PCT Pub. No.: WO2015/195749
PCT Pub. Date: Dec. 23, 2015

(65) Prior Publication Data
US 2017/0137356 A1 May 18, 2017

Related U.S. Application Data

(60) Provisional application No. 62/013,060, filed on Jun. 17, 2014.

(51) Int. Cl.
*C07C 41/03* (2006.01)
*B01J 31/00* (2006.01)
*B01J 31/02* (2006.01)

(52) U.S. Cl.
CPC ........... *C07C 41/03* (2013.01); *B01J 31/0202* (2013.01); *B01J 31/0204* (2013.01); *B01J 31/0212* (2013.01)

(58) Field of Classification Search
CPC .... C07C 41/03; B01J 31/0202; B01J 31/0204
USPC ........................................................ 568/622
See application file for complete search history.

(56) References Cited

U.S. PATENT DOCUMENTS

| | | | |
|---|---|---|---|
| 4,754,075 A | 6/1988 | Knopf et al. | |
| 4,775,653 A | 10/1988 | Leach et al. | |
| 4,820,673 A | 4/1989 | Knopf et al. | |
| 4,835,321 A | 5/1989 | Leach et al. | |
| 5,220,077 A | 6/1993 | Sandoval et al. | |
| 5,627,121 A | 5/1997 | Lin et al. | |
| 2007/0060770 A1 | 3/2007 | Matheson et al. | |

*Primary Examiner* — Sikarl Witherspoon
(74) *Attorney, Agent, or Firm* — Bushman Werner, P.C.

(57) ABSTRACT

A process of preparing an alkoxylation catalyst wherein a catalyst precursor which is formed from an alkoxylated alcohol, calcium hydroxide, carboxylic acid, inorganic acid, and propylene oxide, is mixed with an antioxidant, preferably butylated hydroxyl toluene. A process of alkoxylation using the catalyst of the present invention.

22 Claims, 6 Drawing Sheets

CATALYST COMPOSITIONS, METHODS OF PREPARATION THEREOF, AND PROCESSES FOR ALKOXYLATING ALCOHOLS USING SUCH CATALYSTS

CROSS REFERENCE TO RELATED APPLICATION

This application claims priority to U.S. Application No. 62/013,060 filed on Jun. 17, 2014 the disclosure of which is incorporated herein by reference for all purposes.

FIELD OF THE INVENTION

The present invention is directed to an alkoxylation catalyst composition, a method of preparing same, and alkoxylation processes employing such catalysts. In particular, the present invention is directed to catalyst compositions and methods for alkoxylating alcohols, particularly the ethoxylation of alcohols.

BACKGROUND OF THE INVENTION

The alkoxylation of alcohols can be conducted using various catalysts. For example, a typical method of alkoxylating an alcohol is one employing KOH as a catalyst.

In recent years, the alkoxylation of alcohols has been conducted using alkaline earth metal based catalysts. Such alkaline earth metal based catalysts are disclosed in U.S. Pat. Nos. 4,775,653; 4,835,321; 4,754,075; 4,820,673; 5,220,077; 5,627,121; and U.S. Patent Publication 2007/0060770, all of which are hereby incorporated by reference for all purposes. These alkaline earth metal based catalysts are preferred for alkoxylation reactions, particularly the alkoxylation of alcohols, primarily for their ability to produce what are known as peaked ethoxylates as discussed more fully in the patents and patent applications referenced above. As is well known to those skilled in the art, the peaked ethoxylates impart certain desirable properties for the end use applications such as surfactants, detergents, etc.

In the typical alkoxylation reaction, regardless of the catalyst employed, an alkylene oxide, e.g., ethylene oxide, is reacted with a compound having an active hydrogen atom, e.g., an alcohol. It is to be understood however, that the alkoxylation of other compounds having active hydrogens, such as carboxylated compounds, can also be conducted by this condensation reaction with a suitable alkylene oxide and suitable catalyst.

Typically, the alkylene oxide employed contains from 2 to 4 carbon atoms, more preferably, 2 to 3 carbon atoms. Thus, ethylene oxide and propylene oxide are generally the alkylene oxides chosen in most alkoxylation reactions.

There are several problems posed by alkoxylation reactions, particularly alkoxylation reactions involving alkaline earth metal based catalysts as described in the above listed patents and patent publications. One such problem is the fact that some alkoxylated alcohols are subject to oxidation. Presently, the use of butylated hydroxyl toluene (BHT) as an antioxidant for alkoxylates is added to the final product, i.e., the alkoxylated alcohol, as it is being loaded in to tank cars or other vessels for transportation. The oxidation problem is particularly acute with respect to alcohol alkoxylates containing a high mole content of the alkoxylates. In this regard, such high mole alkoxylates have to be heated to remain liquid and therefore pumpable into tank cars and other containers. The heat needed to maintain the alkoxylates in liquid form further perpetuates their oxidation. Additionally, it is difficult to assure uniform mixing of the antioxidant and the alcohol alkoxylates within the transportation vessel and indeed to a large extent mixing, to the extent it is conducted, is simply a result of the splashing of the liquid in the tank cars, or other transport vessels. It is hoped that this incidental mixing will dissolve the antioxidant before air oxidation can ensue.

Another problem typically encountered during the alkoxylation of alcohols, particularly alcohols having significant vapor pressures at the temperatures of typical alkoxylation reactions, e.g., 150 to 175° C., is reduced head space in the vessel. Because the reaction is conducted in a closed vessel, the high vapor pressure of the alcohols causes the head space pressure of the reactor to be filled with the partial pressure of the alcohol vapor. This alcohol vapor pressure coupled with nitrogen head space pressure, added to the reactor for safety purposes, vastly reduces head space available for the generally gaseous alkylene oxides. The effect is a cascading one since the added alkylene oxide causes the reactor pressure to build up and prevents further addition of alkylene oxide. The result creates difficulty in initiating the reaction and reduces production of the desired alkoxylate.

SUMMARY OF THE INVENTION

In one aspect, the present invention provides a catalyst for use in the alkoxylation of alcohol.

In another aspect, the present invention provides a method for producing a catalyst for use in the alkoxylation of alcohol.

In yet another aspect, the present invention provides a method of alkoxylating unsaturated alcohols, particularly alcohols having a terminal bond, which prevents isomerization resulting in internal double bonds.

These and further features and advantages of the present invention will become apparent from the following detailed description, wherein reference is made to the figures in the accompanying drawings.

DETAILED DESCRIPTION OF PREFERRED EMBODIMENTS

While the present invention will be described with particular respect to the use of alkaline earth metal based catalysts in alkoxylation reactions, it is not so limited. In general, the compositions and methods of the present invention can be used in any catalyzed reaction for the production of alkoxylated alcohols or the like wherein oxidation of the resulting alkoxylates is a problem.

As noted, the present invention finds particular utility with respect to alkoxylation catalysts, methods of preparing same, and methods of alkoxylation, wherein inter alia oxidation of the resulting alkoxylates poses a problem.

Preparation of Catalyst Precursor

Preparation of the catalyst of the present invention begins with preparation of a precursor to the catalyst, herein referred to as Catalyst Precursor. As detailed in U.S. Pat. No. 5,627,121 ('121 Patent), hereby incorporated by reference for all purposes, the Catalyst Precursor is formed by reacting an alkoxylated alcohol mixture having the general formula:

$$R_1\text{-}0\text{-}(C_nH_{2n}0)_pH \quad \quad \quad \text{I}$$

wherein $R_1$ is an organic radical containing from about 1 to about 30 carbon atoms, n is 1-3, especially 2, and p is an integer of from 1-50, with calcium hydroxide, a carboxylic acid, and an inorganic acid. To the mixture is then added propylene oxide.

The alkoxylated alcohol mixture used can be prepared by methods well known in the art for preparing alkylene oxide adducts of alcohols. Alternately, the alkylene oxide adducts can be prepared according to the process of the present invention. The alkoxylated alcohol mixture used in preparing the Catalyst Precursor typically contains free alcohol, the amount and type of which will vary depending upon the source of the alkoxylated alcohol. Generally speaking, the alkoxylated alcohol mixture will contain from about 1% to about 60% by weight free alcohol.

Suitable carboxylic acids are those which have greater miscibility in hydrocarbon solvents than in water. Such carboxylic acids, which may generally be considered fatty acids, have a carbon chain length versus acid functionality which provides their greater miscibility or solubility in hydrocarbons. Non-limiting examples of fatty acids include those natural or synthetic mono-functional carboxylic acids wherein the carbon chain length is greater than about 5 carbon atoms, generally from about 5 to about 15 carbon atoms. Specific examples of such suitable acids include hexanoic, octanoic, nonanoic, 2-ethyl hexanoic, neodecanoic, isooctanoic, stearic, napthanoic, and mixtures or isomers of such acids. While it is preferred that the acids, if used, be saturated, they may optionally contain other functional groups such as hydroxyl groups, amine groups, etc. which do not interfere with the process. It has been found that the use of the fatty acids leads to a better dispersion of the calcium hydroxide and that the active catalyst suspension is more stable in terms of the solids remaining dispersed.

The inorganic acids useful include the acids themselves as well as "acid salts". Thus, non-limiting examples of inorganic acids include sulphuric acid, hydrochloric acid, hydrofluoric acid, phosphoric acid, pyrophosphoric acid, ammonium biflouride, ammonium sulfate, etc. Particularly preferred are the oxy acids, such as sulphuric acid.

In a preferred method of forming the Catalyst Precursor, the calcium hydroxide and the alkoxylated alcohol mixture are charged into a suitable stirred vessel equipped with a reflux condenser. The mixture is stirred for 30 minutes following which the carboxylic acid is added and then stirred for another 30 minutes. Generally, the three components are mixed at room temperature, although higher temperatures can be used. Following dispersion of the calcium hydroxide, an inorganic acid, e.g., sulfuric acid, is introduced into the reaction mixture in an amount sufficient to neutralize at least 25% of the titratable alkalinity present in the reaction mixture. The inorganic acid is added slowly, in two portions, to avoid any sulfation of the alkoxylate. Each of the two portions should be added over the duration of at least 1 hour with at least 45 minutes of stirring between the addition of each portion. Throughout the addition of the sulfuric acid, the temperature should be maintained below 50° C. This can be accomplished by any known method but it in a preferred embodiment, the temperature is maintained using cooling water circulation and controlled addition of the sulfuric acid. It may be necessary to pull a partial vacuum on the reactor during this step as the inorganic acid may be thick and viscous.

Propylene oxide is added under propoxylation conditions to effect propoxylation of at least a portion of the alkoxylated alcohols present in the Catalyst Precursor. Following propoxylation according to the process of the present invention, there is produced an alkoxylated/propoxylated alcohol having the formula $$R_1\text{-}0\text{-}(C_nH_{2n}0)_p\text{—}(C_3H_60)_tH \quad \quad \quad \text{II}$$

wherein n is 1-3, especially 2, p is 1 to 50, and t is from 1 to 15, preferably from 1 to 10, more preferably from 1 to 7. Particularly preferred is an ethoxylated/propoxylated species coming within Formula II wherein $R_1$ contains from 8 to 14 carbon atoms, p is from 2 to 6 and t is from 1 to 3, most preferably from 1 to 1.5. It will be understood that, as in the case of all alkoxylated species of alcohols, there is a distribution of the alkoxy groups, the numbers above referring to the average number of alkoxy/propoxy groups present in the alkoxylated species.

In general the Catalyst Precursor is reacted with the desired amount of propylene oxide at a temperature from about 95 to about 200° C., preferably about 100° C. and from 15 to 75 psig propylene oxide pressure. The mixture can be stripped for about 15 minutes under partial vacuum pressure to remove any volatiles.

Preparation of Catalyst

To prepare the Catalyst of the present invention, the Catalyst Precursor is prepared as a slurry and crystalline BHT is added to the slurry in an amount which results in a 50 to 200 ppm, preferably 50 to 100 ppm, dosage of BHT in the alkoxylated alcohol final product. The BHT is mixed with the slurry at about 25° C. at atmospheric pressure, until it is dissolved.

It will be appreciated that other antioxidants can be used to produce a catalyst with antioxidant properties, e.g., butylated hydroxyanisole, provided the antioxidant in question is not deleterious to human health.

Alkoxylation Processes using the Catalyst of the Present Invention

The Catalyst of the present invention is suitable for use in the alkoxylation of compounds having active hydrogen atoms, e.g., alcohols. The Catalyst is reacted with alkylene oxide and the compound of choice having an active hydrogen atom.

In typical prior art alkoxylation reactions, the reaction is undertaken at temperatures of 150° C. to 175° C. The alkoxylation of alcohols using the improved catalyst of the present invention is performed at significantly lower temperatures, particularly 110° C. to 130° C. This reduction in temperature in turn reduces the vapor pressure within the reactor allowing for more head space in the reactor for the alkylene oxides. The additional room in the reactor means that more alkylene oxide can be added at a faster rate, thus improving efficiency of the process.

Prior art alkoxylation catalysts such as NaOH, KOH, or sodium methoxide, require the additional step of stripping out water or methanol after the addition of the catalyst to the alcohol. The removal of water is important to avoid the formation of polyethylene glycol. This step can be difficult to achieve when alkoxylating light volatile alcohols (such as hexanol or isopentenol) as the water removal process also removes the volatile feed alcohol. The catalyst of the present invention does not require the stripping out of water. The alkoxylation of alcohols using the catalyst of the present invention is thus more efficient and has a higher product yield.

The catalyst of the present invention is particularly suited for the alkoxylation of alcohols having terminal double bonds. Prior art catalysts with high alkalinity, e.g., potassium hydroxide and sodium methoxide, will isomerize the double bond to move it from the terminal position to an internal position. Additionally, prior art catalysts produce significant amounts of polyethylene glycol (PEG) byproduct. The catalyst of the present invention does not interfere with the terminal double bonds and it yields much lower levels of PEG.

The alkoxylated alcohols produced using the catalyst of the present invention are readily transported. Simply heat the product to a pumpible temperature and pump it into the transportation vehicle. There is no need to take any additional steps to prevent oxidation during transportation. The catalyst of the present invention is especially suitable for preparing products which were typically susceptible to oxidation during transportation.

The following, non-limiting examples will demonstrate the use of the catalyst of the present invention in preventing oxidation of an alkoxylated alcohol, in particular ethoxylated alcohol.

EXAMPLE 1

Samples of a C12-C13 alcohol ethoxylate, having 9 moles of ethylene oxide (EO) were prepared using the catalyst of the present invention. The BHT was added in amounts to deliver 50 ppm, 100 ppm, 200 ppm to the finished ethoxylate. These samples were compared to a sample prepared without BHT and to a sample in which 100 ppm BHT was only added to the finished product. The samples were exposed to air in a forced air oven at a temperature of 60° C. for a period of 17 days. Sample aliquots were taken during this time period and analyzed by NMR for evidence of oxidation by-products including aldehydes, esters, acetals/hemi-acetals, and formate esters. The by-products were reported as "moles per 100 moles of ethoxylate" versus the days of oxidation. The totals of these oxidation by-products were plotted on the Y axis in FIG. 1.

Figure 1:
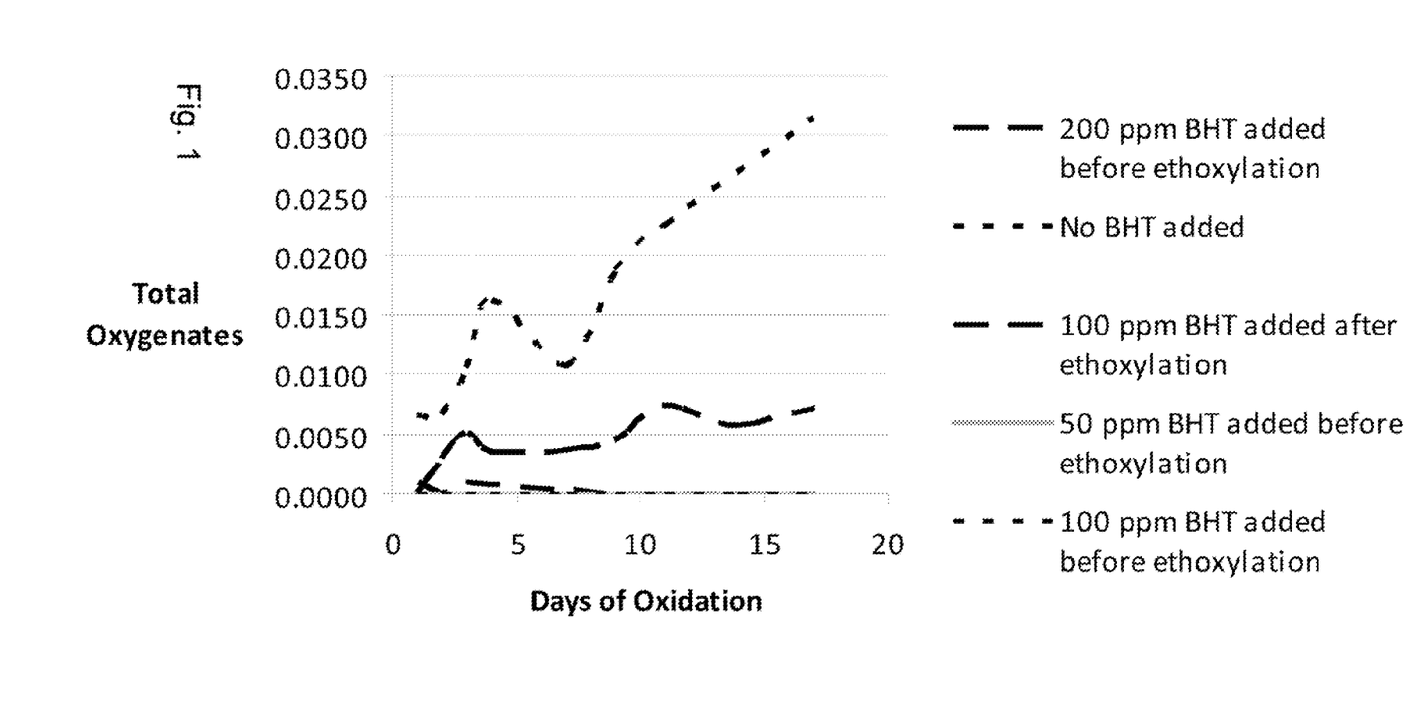
FIG. 1 is a graph of the oxidation results of alcohol ethoxylates prepared using the catalyst of the present invention.
Figure 2:
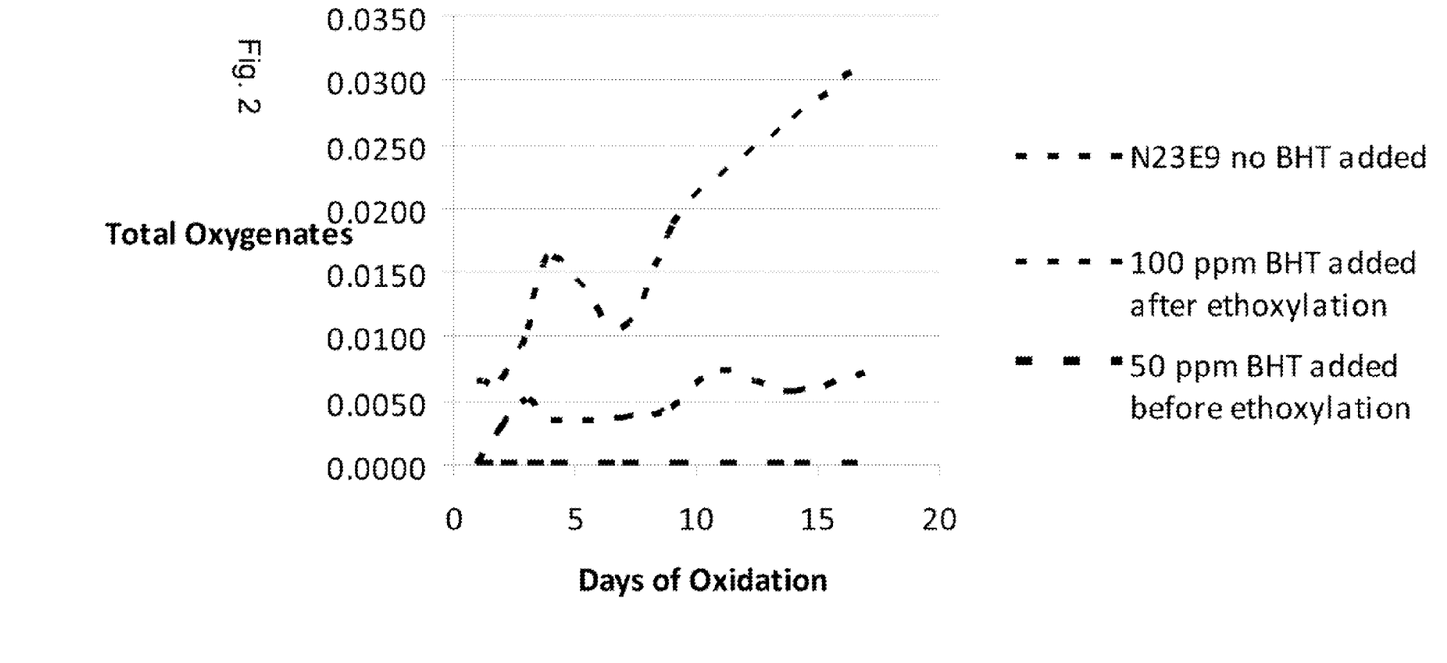
FIG. 2 is another graph of the oxidation results of alcohol ethoxylates prepared using the catalyst of the present invention.

FIG. 2 shows the same data as that in FIG. 1, but compares only the samples in which no BHT was added, the sample in which 100 ppm was added after ethoxylation, and the sample in which 50 ppm BHT was added before ethoxylation.

It can be seen from FIGS. 1 and 2 that the catalyst of the present invention has a significant impact on the prevention of oxidation. The addition of only 50 ppm of BHT before the ethoxylation prevented virtually any oxidation from occurring during the 17 days.

It was surprisingly found that adding the BHT to the alkaline earth metal based catalyst prior to ethoxylation did not impede the performance of the catalyst. Even though BHT has a phenolic hydroxide group, it does not react with ethylene oxide. Without wanting to be bound to the theory, it is believed that this is due to the low alkalinity of the Catalyst Precursor. The catalyst of the present invention allowed the ethoxylation reaction to take place at lower temperatures and significantly reduced the oxidation of the final products. At the same time the performance of the BHT as an anti-oxidant was in no way impeded by exposure to ethylene oxide during the ethoxylation reaction.

The following non-limiting examples demonstrate the alkoxylation of alcohols using the catalyst of the present invention at lower temperatures as well as the minimization of isomerization of terminal double bonds in the alcohol to internal double bonds.

EXAMPLE 2

Two samples of C6 alcohol ethoxylate having 15 moles of EO were prepared using the catalyst of the present invention. The reaction took place in a reactor with the first sample reacted at 110° C. and the second sample reacted at 130° C. The EO was added for 56 minutes and 74 minutes to the first and second samples, respectively. Thus, the further the temperature was reduced, the faster the EO could be added.

EXAMPLE 3

Figure 3:
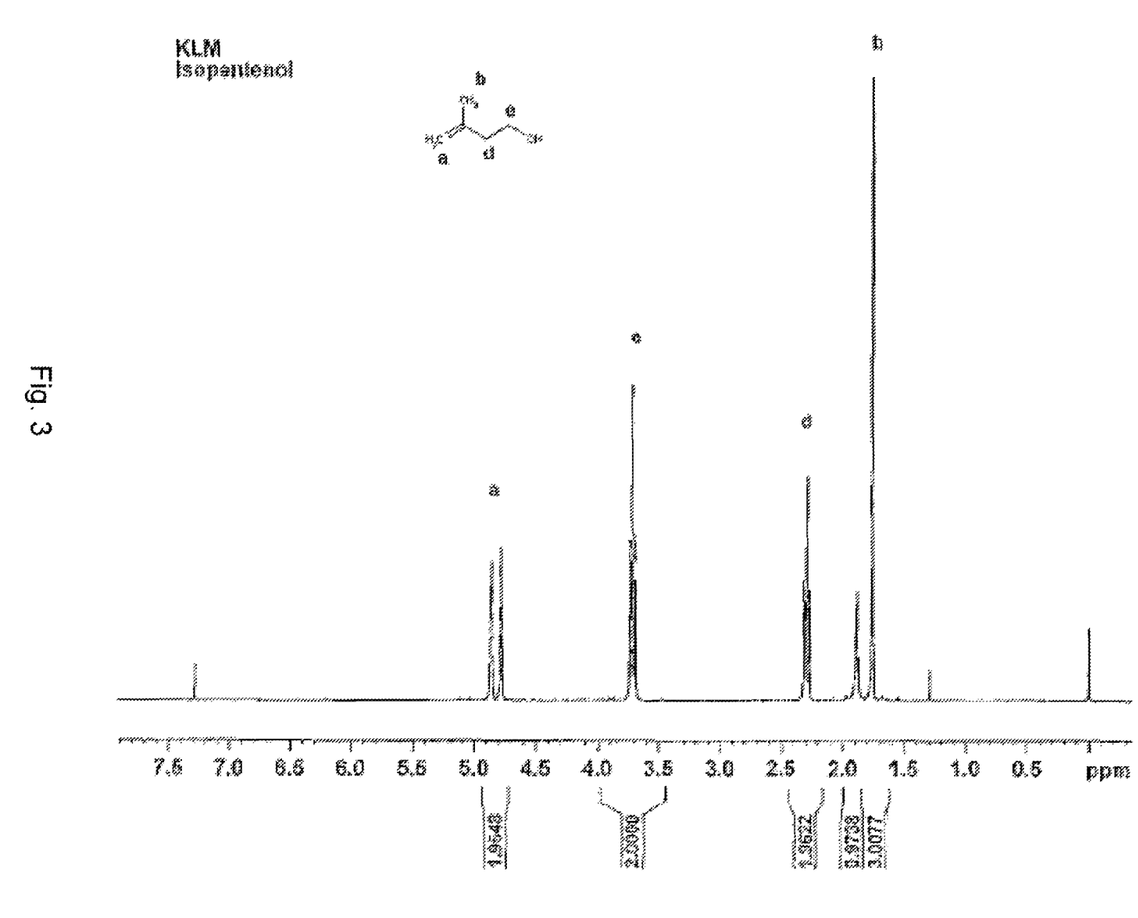
FIG. 3 is an NMR spectrum of isopentenol alcohol.
Figure 4:
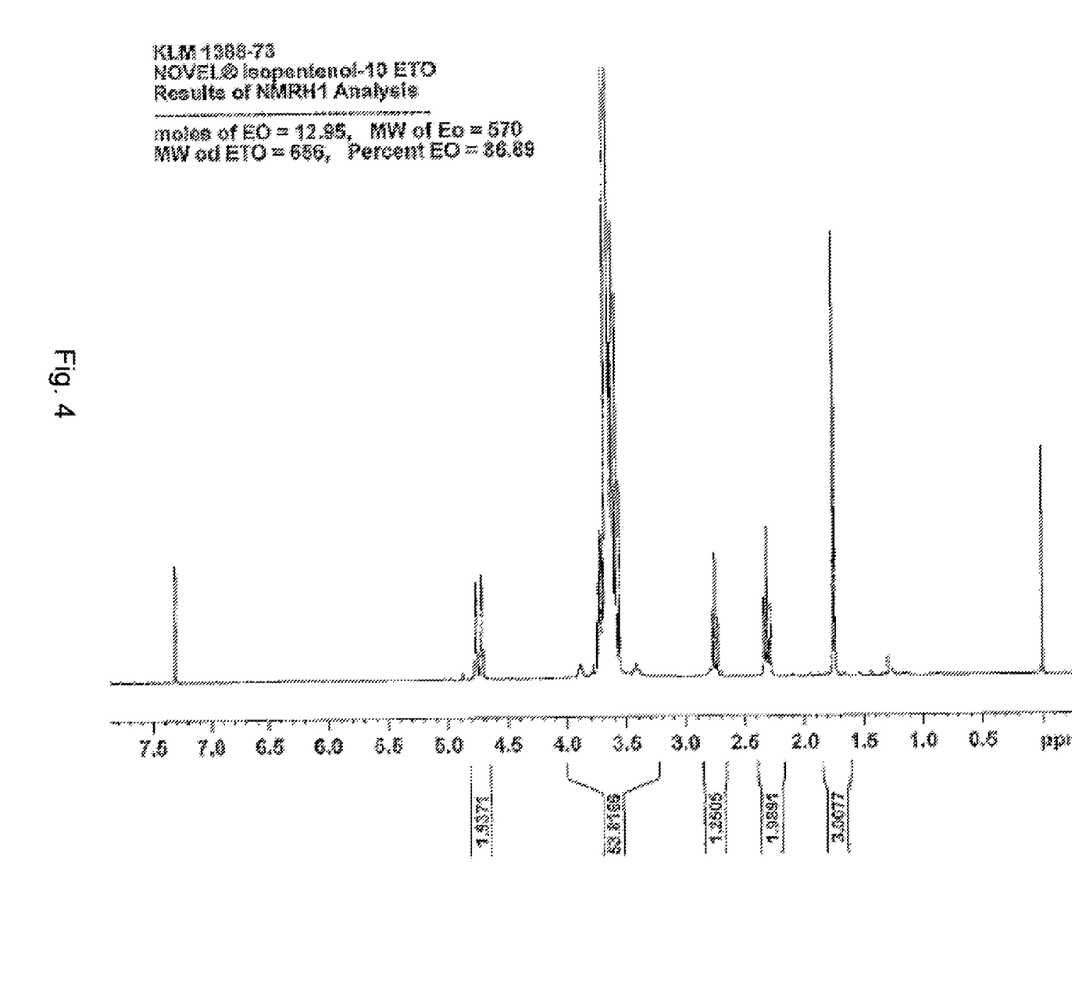
FIG. 4 is an NMR spectrum of isopentenol alcohol with 10 moles of EO, prepared using the catalyst of the present invention.
Figure 5:
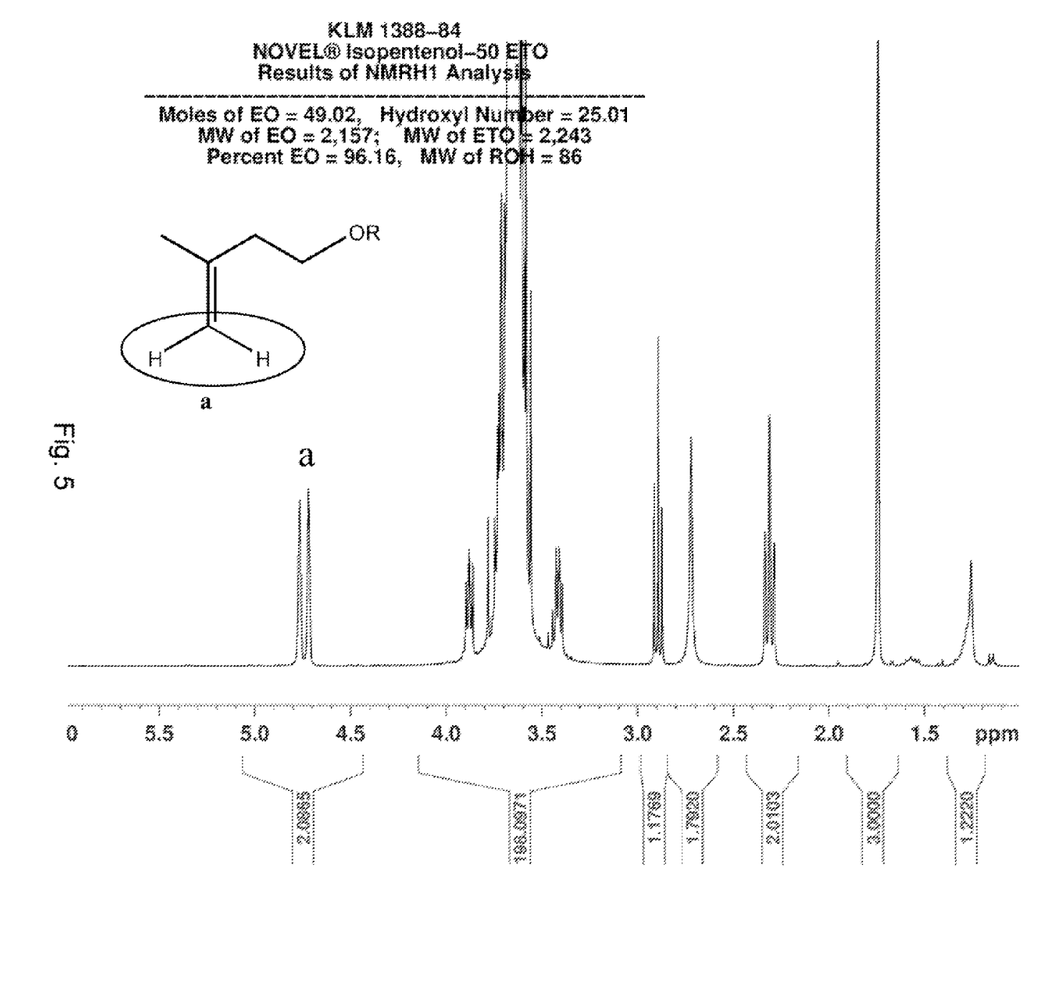
FIG. 5 is an NMR spectrum of isopentenol alcohol with 50 moles of EO, prepared using the catalyst of the present invention.
Figure 6:
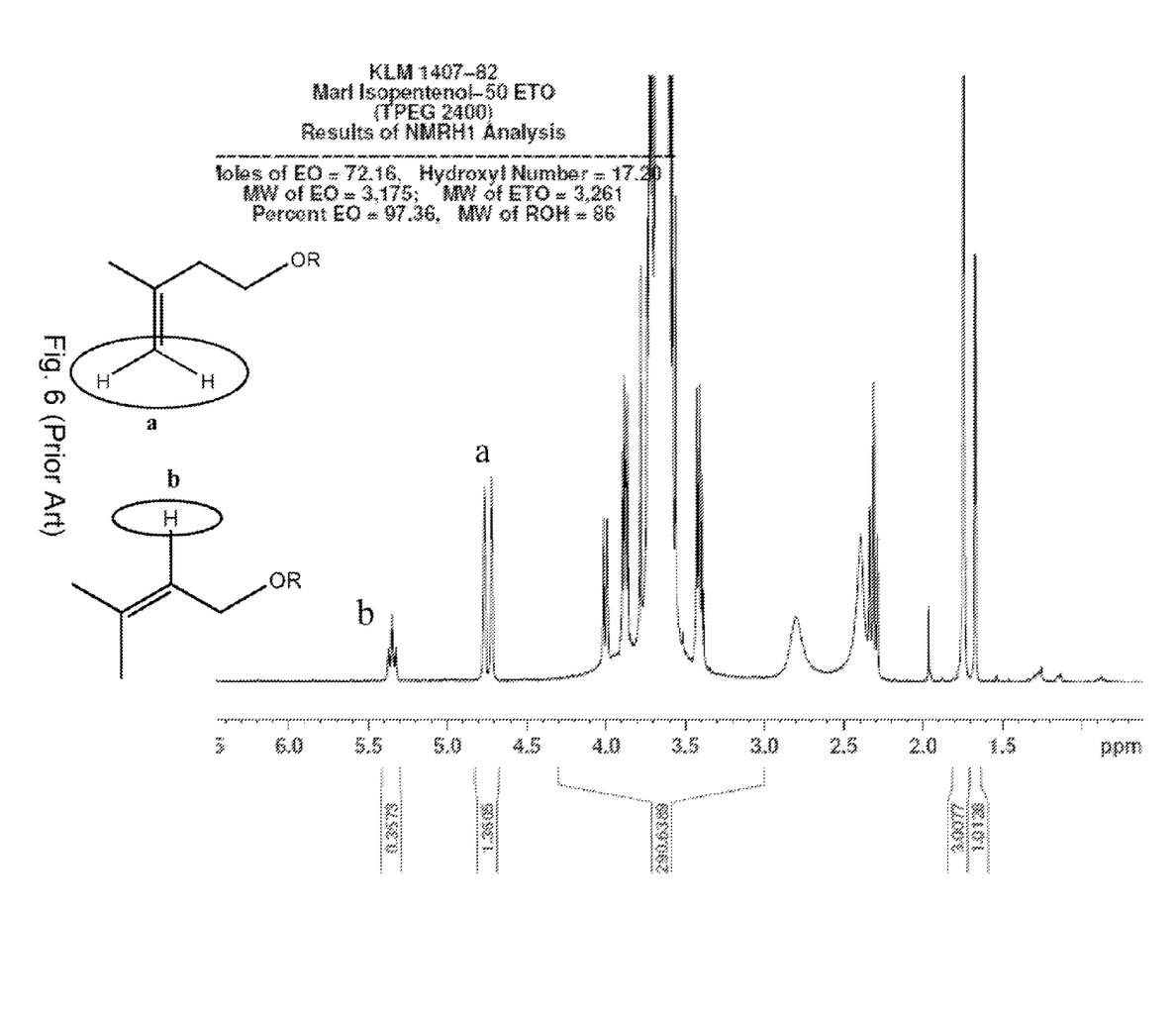
FIG. 6 is an NMR spectrum of isopentenol alcohol with 50 moles of EO, prepared using sodium methoxide catalyst.

Samples of isopentenol having 10 and 50 moles of ethoxylate were prepared using the catalyst of the present invention. The reactions took place at temperatures of 120° C. The amount of catalyst used was 0.2 to 0.4 wt %. FIG. 3 is proton NMR analysis of the isopentenol prior to ethoxylation. FIGS. 4 and 5 are proton NMR analyses of the isopentol ethoxylates having 10 moles and 50 moles, respectively. FIG. 6 shows a proton NMR analysis of the isopentenol ethoxylate with 50 moles of EO made with a prior art sodium methoxide catalyst. Those skilled in the art will recognize that the number of terminal double bonds shown in FIGS. 4 and 5 is the same as in FIG. 3. Thus, the terminal double bonds were preserved during and after the ethoxylation reaction. However, FIG. 6 shows that some of the double bonds have isomerized. In each of the NMR results, for the ethoxylates made with the catalyst of the present invention, the ratio of protons next to the double bonds is consistent that no rearrangement of the double bond is taking place.

The catalyst of the present invention thus provides many significant advantages to the alkoxylation industry. The catalyst prevents oxidation of the alkoxylated alcohols, improves the process efficiency by reducing the temperature, eliminating the need for stripping water, and improving the rates of reaction, prevents isomerization of terminal double bonds in certain alcohols, and improves the transportation of the final product.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A process for preparing an alkoxylation catalyst comprising:
    providing a catalyst precursor formed by reacting an alkoxylated alcohol mixture having the general formula:

$$R_1\text{-}0\text{-}(C_nH_{2n}0)_pH \qquad\qquad\qquad I$$

wherein $R_1$ is an organic radical containing from about 1 to about 30 carbon atoms, n is 1-3, and p is an integer of from 1-50, with calcium hydroxide, a carboxylic acid, an inorganic acid, and propylene oxide under conditions to propoxylate at least a portion of the alkoxylated alcohols; and adding an antioxidant to said catalyst precursor to produce an alkoxylation catalyst.

2. The process of claim 1, wherein said antioxidant is butylated hydroxyl toluene (BHT).

3. The process of claim 1, wherein said antioxidant is butylated hydroxyanisole.

4. The process of claim 1, wherein n is 2.

5. The process of claim 1, wherein the alkoxylated alcohol mixture contains 1-60 wt % free alcohol.

6. The process of claim 1, wherein the carboxylic acid has from about 5 to about 15 carbon atoms.

7. The process of claim 1, wherein the carboxylic acid is selected from a group consisting of hexanoic acid, octanoic acid, nonanoic acid, 2-ethyl hexanoic acid, neodecanoic acid, isooctanoic acid, stearic acid, napthanoic acid, and mixtures of isomers of such carboxylic acids.

8. The process of claim 1, wherein the inorganic acid is selected from the group consisting of sulphuric acid, hydrochloric acid, hydrofluoric acid, phosphoric acid, pyrophosphoric acid, ammonium bifluoride, and ammonium sulfate.

9. The process of claim 1, wherein the inorganic acid is sulphuric acid.

10. The process of claim 1, wherein the inorganic acid is reacted at a temperature less than 50° C.

11. The process of claim 1, wherein propyleneoxide is added in mole amounts from 1-15.

12. The process of claim 1, wherein the propylene oxide is reacted at a temperature of from about 95° C. to about 200° C.

13. The process of claim 10, wherein the propylene oxide is reacted at a temperature of about 100° C.

14. The process of claim 1, wherein the catalyst precursor is prepared as a slurry.

15. The process of claim 1, wherein the antioxidant is mixed at a temperature of about 25° C.

16. An alkoxylation process comprising:

providing a catalyst precursor formed by reacting an alkoxylated alcohol mixture having the general formula:

$$R_1\text{-}0\text{-}(C_nH_{2n}0)_pH \qquad\qquad\qquad I$$

wherein $R_1$ is an organic radical containing from about 1 to about 30 carbon atoms, n is 1-3, and p is an integer of from 1-50, with calcium hydroxide, a carboxylic acid, an inorganic acid, and propylene oxide under conditions to propoxylate at least a portion of the alkoxylated alcohols;

adding an antioxidant to said catalyst precursor to produce an alkoxylation catalyst; and reacting in the presence of said alkoxylation catalyst a reactant comprising a compound having an active hydrogen atom, and an alkylene oxide under alkoxylation conditions to produce an alkoxylated derivative of said reactant.

17. The process of claim 15, wherein said antioxidant is butylated hydroxyl toluene (BHT).

18. The process of claim 15, wherein said antioxidant is butylated hydroxyanisole.

19. The process of claim 15, wherein said compound having an active hydrogen atom is an alcohol.

20. The process of claim 15, wherein said reaction of the reactant in the presence of the catalyst takes place at temperatures from about 110° C. to about 130° C.

21. The process of claim 15, wherein the antioxidant is added in an amount to produce 50-200 ppm BHT in the alkoxylated derivative of the reactant.

22. The process of claim 20, wherein the antioxidant is added in an amount to produce 50-100 ppm BHT in the alkoxylated derivative of the reactant.

* * * * *